United States Patent [19]

Heijenga et al.

[11] 4,428,907
[45] Jan. 31, 1984

[54] DETECTOR FOR DETECTING AIR COMPONENTS

[75] Inventors: Berend Heijenga, Sleen; Hubertus E. Hilbrink, Apeldoorn; Henri F. Klaij, Enschede, all of Netherlands

[73] Assignee: Nederlandse Centrale Organizatie voor Toegepast Natuurwetenschappelijk Onderzoek, The Hague, Netherlands

[21] Appl. No.: 237,492

[22] Filed: Feb. 23, 1981

[51] Int. Cl.³ ................. G01N 31/06; G01N 31/22
[52] U.S. Cl. .................... 422/61; 55/DIG. 33; 55/DIG. 34; 55/DIG. 35; 128/202.22; 422/83; 422/86; 422/88
[58] Field of Search .................... 422/61, 58, 59, 83, 422/305, 165, 86, 88; 128/202.22; 55/DIG. 33, DIG. 34, DIG. 35

[56] References Cited

U.S. PATENT DOCUMENTS

| | | | |
|---|---|---|---|
| 2,908,555 | 10/1959 | Grosskopf | 422/86 |
| 3,689,224 | 9/1972 | Agnew et al. | 422/61 |
| 3,799,742 | 3/1974 | Coleman | 422/61 |
| 3,955,931 | 5/1976 | Thompson | 422/165 |
| 4,246,229 | 1/1981 | McBride et al. | 422/165 |
| 4,272,479 | 6/1981 | Huneke et al. | 422/61 |
| 4,300,910 | 11/1981 | Pannwitz | 422/61 X |

Primary Examiner—Michael S. Marcus
Attorney, Agent, or Firm—Beehler, Pavitt, Siegemund, Jagger & Martella

[57] ABSTRACT

The invention provides a detector for detecting air components, e.g. contaminations, and in particular noxious or poisonous contaminations, which device comprises a housing in which an air pervious carrier containing a first reagent is arranged, this detector being adapted to draw air to be tested through said carrier so as to expose this reagent to the air, this reagent being influenced by the components to be detected, which carrier is to be contacted with a second reagent which, together with the first one, can bring about a color reaction depending on the fact whether the first reagent has been influenced or not. The housing forms, in the operative condition, an integral unit, an air- and liquid-tight container with a rupturable wall and containing a not contaminated liquid contributing to said color reaction being arranged within said housing, the latter being, furthermore, provided with a yieldable wall portion and a plurality of piercing pins arranged in such a mutual spatial relationship that the container can be pierced by pressing inwards said wall portion, so as to moisten said reagent carrier with the liquid from said container. In particular the second reagent can be contained in a similar second carrier which is normally eparated from the first one but is contacted therewith when pressing inwards said wall portion.

24 Claims, 3 Drawing Figures

U.S. Patent  Jan. 31, 1984  4,428,907
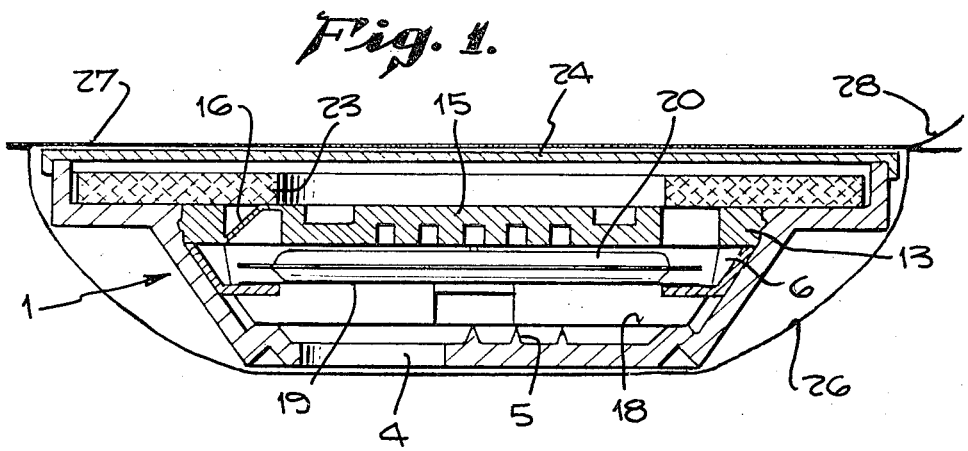
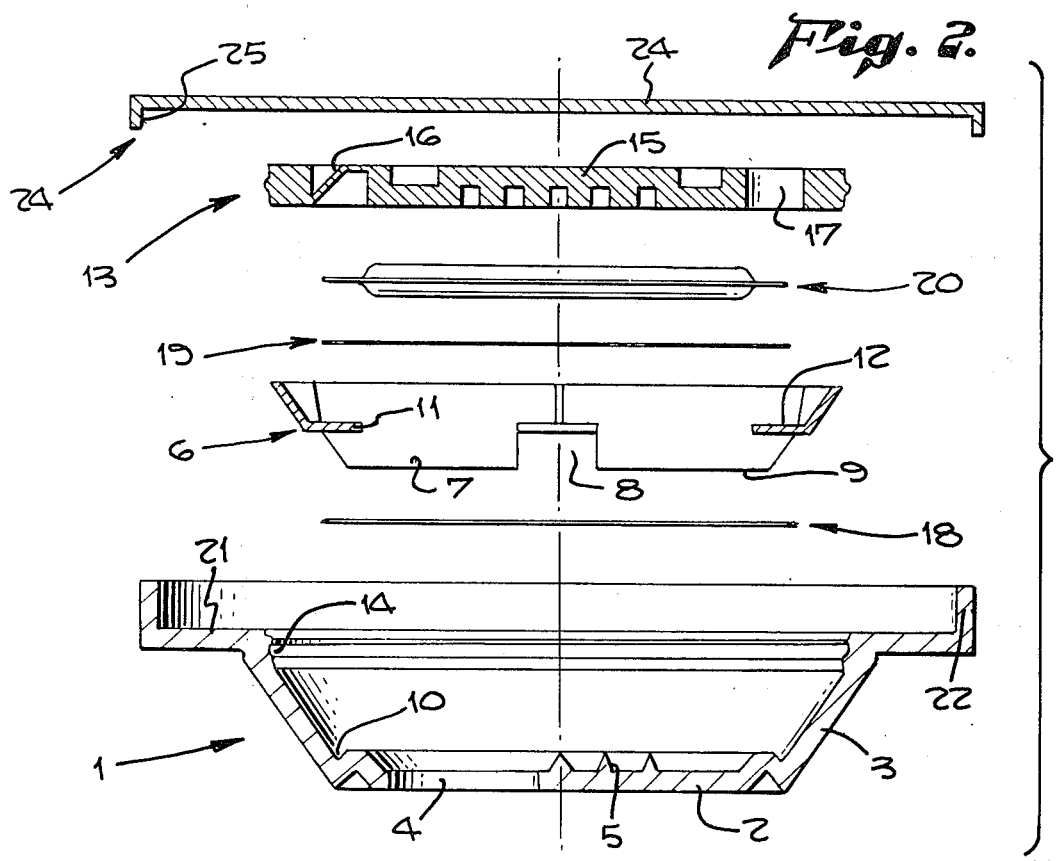
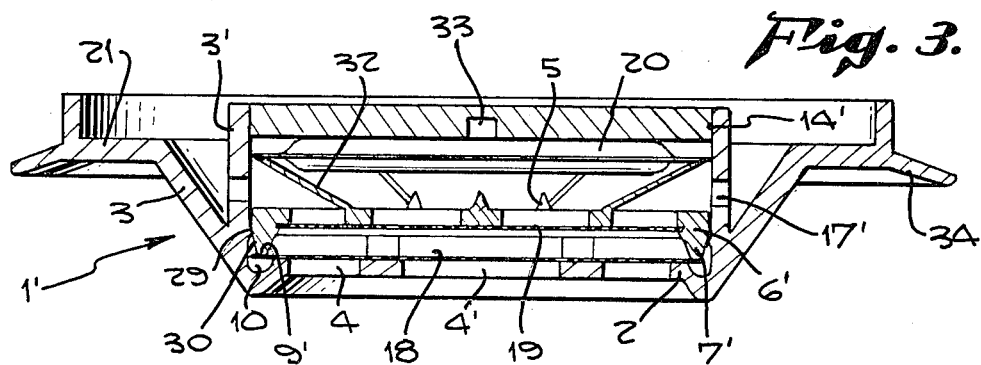

DETECTOR FOR DETECTING AIR COMPONENTS

In many circumstances it is desirable to have available cheap detection means, allowing, in a simple manner, and without having to use specialised knowledge and/or expensive apparatus, to determine in situ whether determined threshold concentrations of poisonous substances in the air are exceeded, in particular in view of taking or cancelling protective measures.

This is, for instance, useful for spaces in which poisonous substances are prepared or stored, for hothouses in which poisonous substances are sprayed, and, of course, for military purposes. When working in an environment in which the air comprises or can comprise poisonous substances, it is generally compulsory to wear gas masks and, as the case may be, also protective clothing, including gloves. Gas masks, however, impede vision and respiration, and protective clothing and gloves will substantially reduce the reedom of movement, which will have a very unfavourable influence on the physical activity and well-being of the persons which have to work therewith. It is, therefore, important to relieve the protective measures as soon as the danger of poisoning has disappeared. Also for detecting nonpoisonous components, such as, for instance, ethanol in exhaled air, there is a need for a simple detector.

Such detectors should satisfy the requirement of being manageable in a simple manner, even with the gloved hand, of requiring little space, of being cheap and being adapted to be manufactured as a disposable article, but being, nevertheless, fully dependable.

In NL-A No. 70 13 950 a detector for enzymostatic substances is described, which substances are present, for example, in insecticides, nerve gases etc., said detector comprising a housing provided with air passages, in which housing an air pervious carrier, in particular a sheet of filter paper, comprising a first reagent is arranged, and the air to be tested is to be sucked through said carrier so as to expose said reagent to this air, which reagent is influenced by the undesired components to be detected, and said carrier is to be contacted with a second reagent which is adapted to produce, together with the first reagent, a colour reaction which depends on the first reagent having been attacked or not, said second reagent also being provided on a sheet of filter paper which is arranged in a second housing part, said housing part being adapted to be placed on the housing part containing the first carrier in such a manner that both carriers can be contacted with one another, which carriers are, then, to be moistened with water so as to bring about the reaction.

This known detector is not suitable for the above-mentioned purposes. Passing the air through the detector is to be brought about by means of an air pump, and the detector can be contacted by the surrounding air already before the air is sucked through. A very important disadvantage is that the reagent carriers must be moistened, which is to be done with water from the environment which, itself, can contain the components to be detected, and this often for a longer time than the surrounding air, so that a colour reaction occurs even if the concentration of the components in question in the air have already decreased below the threshold value. It is, moreover, very cumbersome to handle such a detector with gloved hands, and, moreover, the housing consisting of two pieces is relatively voluminous. The durability of the reagents is, furthermore, restricted, since they are not shielded from the surroundings.

The invention envisages to provide a detector of the kind mentioned above which does not have these disadvantages. To that end the detector according to the inventin is characterised by a housing forming, in the operative condition, an integral unit, by a liquid- and air-tight container with an easily rupturable wall arranged inside said housing near the carrier for the first reagent, and filled with not contaminated reagents or dissolving liquid, by an inwardly yieldable wall portion situated near said container and adapted to be contacted with said container, and by a plurality of piercing pins arranged on or in front of said yieldable wall portion, so that, when pressing inwards said wall portion, the container wall is ruptured so as to moisten the reagent carrier with the liquid from this container, and one or more detectors can be enclosed in a gas- and liquid-tight rupturable envelope.

In particular the second reagent, which will produce with the first one a colour reaction, will be provided on or in a second plane carrier which is normally kept separated from the first carrier, and is, in particular, made of filter paper, which carriers are to be contacted with one another and are to be moistened with a suitable liquid, and, according to the invention, the second carrier is supported at a small distance from and parallel to the first one inside said housing, this in such a manner that, when pressing said yieldable wall portion inwards, both carriers are contacted with one another, the container being filled with a suitable moistening agent, and in particular with pure water.

Such a detector takes very little space, since the housing, in the operative condition, consists of one integral piece which, moreover, facilitates handling, as the only intervention to be made is pressing inwards the yieldable wall portion which can be done in a simple manner also with the gloved hand. The whole assembly is enclosed in an envelope protecting against environmental influences, which can be easily ruptured also with the gloved hand, so that such detectors can be stored for a long time without losing their activity. A special security against influences disturbing the dependability is obtained because the moistening liquid, which may contain, if desired, the second reagent, is comprised in a fully shielded manner in a separate container. Packing liquids in a sterile manner is known from the pharmaceutical industry, and does not provide special difficulties.

In particular the housing is provided with at least one collar or seat fitting in the air suction opening of a gas mask or gas mask filter, so that sucking air through the first reagent carrier will be brought about in a very simple manner. This seat can, for instance, be shaped as a conical surface fitting in openings of different diameter so as to provide an adaptation to different gas mask types, and it is also possible to provide a special seat for nonregular gas mask types, for instance at the other side of the housing. It is also possible to fix such a detector to a stick or the like, and to swing it through the air so as to obtain the required amount of air flowing through. This will, in particular, be done if, for instance, the contents of a storage vessel or space are to be investigated from the outside.

In an embodiment which can easily be manufactured the first reagent carrier is clamped between a bottom rim of the housing and an insert, the latter being provided with support surfaces for supporting the liquid container and, as the case may be, a second reagent carrier, said insert being adapted to be fixed in the housing by means of a clamping ring, and, in particular, the yieldable wall part is connected to said clamping ring by means of yielding and, if required, rupturable lips. Such parts can be manufactured in a simple manner from plastics, and can be assembled very quickly.

The piercing pin or pins are, in particular, provided at the bottom of the housing, which bottom is provided with air passages, which pins are, in particular, provided on the spoke-like wall portions between said passages.

In order to prevent the unintentional rupturing of the liquid container, a removable lid is preferably provided on the housing which, in particular, tightly fits on the rim of the housing.

In order to protect the reagents provided on a carrier against regression, it is advisable to provide a drying means which, in particular, is shaped as a flat ring or disc consisting of or comprising an absorbing material, which, in particular, can be situated within the protecting lid, and, for instance, can annularly surround the yieldable wall portion. Such a ring will, moreover, provide an additional protection of the yieldable wall portion since the forces exerted on the protective lid which, itself, generally consists of a thin plastic plate, can be diverted thereby towards the housing.

Such a detector can be used, besides for the purposes mentioned in the above-mentioned prior patent application, also for detecting any component in air for which a suitable reagent exists.

The invention will be elucidated below in more detail by reference to a drawing, showing in:

FIGS. 1 and 2 a cross section and an exploded view respectively of a first embodiment of the detector of the invention; and FIG. 3 a cross section of a second embodiment thereof.

The gas detector shown in the drawing comprises a box-shaped housing 1 with a bottom 2 with a circular periphery joining a conical lateral wall 3. The bottom 2 comprises uniformly distributed air passages 4, and the intermediate spokes are provided with piercing pins 5.

Inside the housing 1 an insert 6 is placed, having oblique lips 7 bearing against the lateral wall 3 of the housing 1, and being mutually separated by gaps 8, which lips ensure a good fitting against the lateral wall 3. The lower edges 9 of the lips 7 fit in a circumferential groove 10 of the bottom 2. The insert 6 is, furthermore, provided with a plurality of inwardly directed lateral lips 11 with a plane upper surface 12.

On the insert 6 bears a clamping ring 13 which is fixed on the housing 1 behind an incision 14. A pressure plate 15 is connected to the ring 13 by means of a plurality of yieldable and, as the case may be, rupturable lips 16, between which lips air openings are present.

On the rim of the bottom 2 lies a piece of reagent paper 18 which, furthermore, is pressed by the lips 7 of the insert 6 into the groove 10. On the lateral lips 11 of the insert 6 lies a second piece of reagent paper 19 which is maintained by the insert 6 at some distance from the reagent paper 18.

The reagent paper 18 consists, for example, of filter paper of similar absorbent carrier material with a low air flow resistance, containing the enzyme butyryl cholesterinase, the reagent paper 19 containing, for instance, 2,6 dichloro-indophenyl acetate. This enzyme is sensitive for certain poisonous substances, such as, for instance, substances used as insecticides, nerve gases and the like, which substances inactivate the enzyme. The second reagent will be discoloured under the influence of the active enzyme, so that, from the colour, the presence of the enzyme attacking substances can be derived. As a colour regeant also a mixture of, for instance, α-naphtyl acetate and diazonium blue can be used. All this has already been described in the older patent application No. 70 13 950. Of course similar colour reactions can also be obtained by means of other reagents which are sensitive for similar or other components present in the air.

On the surface 12 of the lateral lips 11 rests a gas- and liquid-tight liquid container 20 consisting of a gas- and liquid-tight foil material, e.g. metallic foil coated with plastics or the like. This container is filled with a liquid required for or enhancing the reaction, and can in the considered case consist of, for instance, pure water which is then to be used for moistening both reagent carriers 18 and 19 so as to bring about hydrolysis, or to mix the reagents with one another.

As Seen in the drawings, the yieldable wall 24, the container 20 and the carriers 18, 19 are of generally planar configuration and are normally supported in the housing 1 in spaced parallel relationship. The housing is preferably disc shaped and the yieldable wall, the container and the carriers are spaced along the axis of the disc, which axis is indicated by the vertical dotted line in FIG. 2, and the container is disposed between the yieldable wall and the carriers.

Around the pressure plate 15 and on a plane collar portion 21 inside an upright flange 22 of the housing rests a disc of moisture absorbing material, e.g. paper or textile, impregnated with silica gel. This assembly is covered by means of a protective lid 24 having a lateral rim 25 which tightly fits on the flange 22 of the housing 1. This lid prevents that the pressure plate 15 will be untimely pressed inwards. Moreover the disc 23 can divert the forces exerted thereon towards the housing 1 when the lid 24 is pressed inwards.

The housing 1 filled and closed in this manner is enclosed in a gas- and liquid-tight envelope 26 made of metallic foil and/or plastics which is closed by means of a cover layer 27, which cover layer can be pulled away by means of a pulling tab 28. In this manner the gas detector is kept separated from the surroundings in a gas- and liquid-tight manner, and the drying means 23 keeps the interior of the envelope dry. The lid 24 protects the liquid container 20 against damage by forces exerted on the whole assembly.

In order to use the gas detector, at first the envelope 26 is pulled open, after which the lid 24 and the drying means 23 are removed. This can be done with gloved hands, since the pulling tab 28 and the lateral flange 25 of the lid 24 provide sufficient hold.

The housing 1 is, then, arranged in the suction opening of a gas mask filter box, either with the conical wall 3 or with the flange 23. The conical wall 3 is, for instance, suitable for the current European gas masks, and the flange 22 is adapted to American gas masks. In this manner one single detector is made suitable for all the gas mask types now currently in use.

When breathing, the air is sucked inwards through the reagent paper 18 in which the components to be detected are absorbed. After a certain suction time the detector is removed again from the gas mask, and then the pressure plate 15 is pressed inwards. The liquid container is, then, pierced by the pins 5 so that the reagent papers 18 and 19 are moistened. At the same time these papers are pressed against one another. After a given reaction time it can be established on the basis of the colour change whether the threshold concentration of the components in question has been exceeded.

Such detectors are not very voluminous and are very light, so that the user of a gas mask can take with him a sufficient number thereof. Since the detectors contain all the components required for the reaction, including the moistening liquid, no other interventions are required than opening the envelope and rupturing the liquid container, and finally sucking through a given amount of air with the aid of a gas mask.

The detector according to the invention comprises a small number of parts which can be manufactured and assembled in a simple manner, so that it becomes possible to manufacture large numbers thereof at a relatively low price. Moreover such detectors are enclosed in such a manner that they are tenable very long.

It is also possible to mount such a detector, e.g. in a suitable seat, on a rod, and to swing it through the air to be tested. This can, for instance, be done for testing the contents of tanks or storage spaces in which harmful gases or vapours can be present, and the rod can be inserted inwardly through a manhole or door opening.

Such a detector can also be used with other reagents than those mentioned above, for instance for being used to detect other air components. It is, for instance, also possible to use only one reagent paper 18, and to dissolve the other reagent bringing about a colour reaction in the liquid in the liquid container 20. Furthermore it is possible to provide both reagents in one piece of filter paper if they do not react in the dry condition, which is made possible, in particular, since the contents of the envelope 26 are kept dry. Such a detector can also be used, for instance, for detecting alcohol in exhaled air and for similar purposes.

It is, for the rest, not always necessary to enclose such detectors in an envelope 26, and it is often also possible to enclose a plurality of detectors together in a moisture- and gas-tight manner.

The embodiment shown in FIG. 3 mainly corresponds to that of FIGS. 1 and 2. Similar parts have been indicated by te same reference numerals, and modified parts by primed ones.

The housing 1' comprises an internal cylindrical sleeve or barrel 3' which is integrally connected to the conical outer wall 3, in which sleeve the essential elements are arranged. The bottom of the housing 1' is provided with an additional central opening 4' for improving the visibility of the reagent paper 18. The pins 5 are no longer connected to the bottom 2, as will be described below.

The insert 6' of this embodiment is provided with a plurality of teeth 7' which are narrower than the lips 7 of FIGS. 1 and 2. Moreover, in de normal position shown, the extremities 9' of the teeth 7' do not extend into the circumferential groove 10, since the insert 6' is maintained in the position shown by means of a detent ridge 29 bearing on chamfered surface parts 30 of the teeth 7'. The lower faces 9' of the teeth 7' keep the reagent paper 18 slightly pressed against the upper surface of the bottom 2.

The second reagent paper 19 is supported by the insert 6' which is, for instance, provided with a circumferential groove 31 for fixing the sheet 19. Alternatively, the insert may comprise two parts between which a sheet of reagent paper can be clamped.

The piercing pins 5 are, now, provided on the insert 6' at the upper side thereof, so that it is no longer necessary, as in the first embodiment, to pierce also two layers of reagent paper before piercing the container 20. In order to prevent that the latter will touch the pins 5, the insert 6' is provided with a plurality of resilient and/or rupturable fingers 32, and the rim part of the container 20 bears on the extremities of these fingers, the container thus being kept at a suitable distance from the sharp points of the pins 5.

The pressure plate 15 is, now, directy connected to the sleeve 3' by means of a snap lock 14'. The fingers 32 press the container 20 against the lower surface of this plate 15.

When pressing the plate 15 inwards, the snap lock 14' is released, and the container is pressed against the fingers 32. The latter will yield or break, and then the container 20 is pressed against the pins 5 which will pierce the container wall, and will, eventually, enter recesses 33 in the plate 15. Subsequently the insert 6' is pressed downwards, and then the teeth 7' will slightly be pressed inwards so as to slide past the ridge 29. The sheet 18 is tightened by the teeth 7' entering the groove 10, and both sheets 18 and 19 will then be contacted with one another.

The pressure plate 15 shown has no air passages 17 as in the case of FIGS. 1 and 2, but air passages 17' are provided in the sleeve 3'. However it is also possible to provide passages 17 in the plate 15.

The housing 1' is provided with an extending circumferential rim 34, which serves as a handle when placing the detector on a gas mask, and instead thereof one or more discrete handle parts can be provided. It will be clear that such parts can also be provided in the case of FIGS. 1 and 2.

It will be clear that the pins 5 can also be provided on the plate 15, which should, then, also be provided with the fingers 32, and then a simpler insert can be used.

Many other modifications are possible, and in particular features of the embodiment of FIG. 3 may be used in the embodiment of FIGS. 1 and 2 and vice versa.

We claim:

1. In a detector for detecting the presence of given components in air, comprising a housing provided with preformed air passages, air pervious carrier means containing at least a first reagent, said carrier means being arranged such that the air to be tested is to be passed through said carrier means in order to expose said first reagent to the air, which first reagent is influenced by the components to be detected, a second reagent present within said housing such that when said first carrier means is contacted with said second reagent a color reaction may be brought about depending on whether the first reagent has been influenced or not, the improvement comprising: a housing which forms, in the operative condition, an integral unit, an air- and liquid-tight container having an easily rupturable wall arranged within the housing and in close proximity to said carrier means for the first reagent, said container being filled with non-contaminated liquid, an inwardly yieldable wall portion situated near said container and adapted to be contacted with said container, said container, said yieldable wall and said carrier being each of generally planar configuration and spaced parallel arrangement with respect to one another, and a plurality of piercing pins cooperating with said yieldable wall portion so that, when pushing inwards said wall portion, the container wall is ruptured by said pins so as to moisten said reagent carrier means with the liquid from said container, said liquid bringing said second reagent into contact with said first reagent.

2. The detector of claim 1 wherein said housing has a bottom provided with preformed air passages and said piercing pins are arranged on housing bottom.

3. The detector of claim 1, wherein said piercing pins are arranged on said yieldable wall portion.

4. The detector of claim 1, wherein said piercing pins are provided on said insert.

5. The detector of claim 1 further comprising collapsible support means for the container.

6. The detector of claim 1, further comprising a protective lid removably attached to said housing for shielding said yieldable wall portion and a flat element carrying a drying substance interposed between said protective lid and said yieldable wall portion.

7. The detector of claim 1 wherein said housing is generally disk shaped and said yieldable wall, said container and said carrier means are spaced along the axis of said disc.

8. The detector of claim 1 wherein said container is disposed between said yieldable wall and said carrier means.

9. The detector of claim 1, wherein the housing is enclosed by a gas- and liquid-tight and rupturable envelope.

10. The detector of claim 1 wherein one housing is provided with at least one collar or seat defined on the exterior of said housing and adapted to be located within an air suction opening of a gas mask or gas mask filter.

11. The detector of claim 1, further comprising an insert adapted to clamp said first reagent carrier against said housing bottom, which insert is provided with supporting surfaces for supporting the liquid container, and clamping means for fixing the insert in said housing.

12. The detector means of claim 1 wherein said carrier means comprises one or more sheets of filter paper.

13. The detector of claim 1 or 9, in which said second reagent is applied on a second reagent carrier means separate from said first reagent carrier means and said second carrier means is supported within the housing such that, when pressing inwards the yieldable wall portion, both reagent carrier means are brought into contact with one another and are moistened with said non-contaminated liquid released from said container.

14. The detector of claim 1 or 9 wherein said second reagent is located in said non-contaminated liquid in said container.

15. The detector of claim 10, wherein said seat is a conical surface adapted to fit into openings of different diameters.

16. The detector of claim 11, wherein said yieldable wall portion is a part of said clamping means.

17. The detector of claim 11, wherein said clamping means comprise a clamping ring, said clamping ring supporting said yieldable wall portion by means of yieldable and/or rupturable lips.

18. The detector of claim 11, wherein said clamping means for the insert allow it to be displaced towards the reagent carrier by the yieldable wall portion.

19. The detector of any one of claims 9, 10 or 11 further comprising a protective lid removably attached to said housing for shielding said yieldable wall portion.

20. The detector of claim 19, wherein said cover is provided with a clamping rim dimensioned to make a friction fit with said housing.

21. The detector of claim 9 further comprising a drying agent provided within the envelope.

22. The detector of claim 21, wherein said drying agent comprises a flat element made of an absorbing material impregnated with a drying substance.

23. The detector of any one of claims 1, 9, 10, 11, 12 or 17, wherein said housing is provided with outwardly extending handle means.

24. The detector of claim 10, wherein said supporting surfaces also support a second reagent carrier.

* * * * *